United States Patent [19]

Seckinger et al.

[11] Patent Number: 5,665,681

[45] Date of Patent: Sep. 9, 1997

[54] 2-PHENYL-7-CHLORO-PERHYDROIMIDAZO [1,5A]PYRIDINES

[75] Inventors: Karl Seckinger, Riegel, Germany; Sasank Sekhar Mohanty, Arlesheim; Karlheinz Milzner, Basel, both of Switzerland; Fred Kuhnen, Weil am Rhein, Germany

[73] Assignee: Sandoz Ltd., Basel, Switzerland

[21] Appl. No.: 492,687

[22] Filed: Jun. 20, 1995

[30] Foreign Application Priority Data

Jun. 23, 1994 [GB] United Kingdom ............... 9412603

[51] Int. Cl.[6] ............... A01N 43/90; C07D 471/04
[52] U.S. Cl. ............... 504/246; 546/121
[58] Field of Search ............... 546/121; 504/246

[56] References Cited

U.S. PATENT DOCUMENTS 5,482,921  1/1996  Seckinger ............... 504/246

FOREIGN PATENT DOCUMENTS

| 0070389 | 1/1983 | European Pat. Off. . |
| 0384973 | 9/1990 | European Pat. Off. . |
| 0468924 | 1/1992 | European Pat. Off. . |

Primary Examiner—C. Warren Ivy
Assistant Examiner—Evelyn Huang
Attorney, Agent, or Firm—Robert S. Honor; Carl W. Battle; Michael P. Morris

[57] ABSTRACT

The invention discloses compounds of formula I

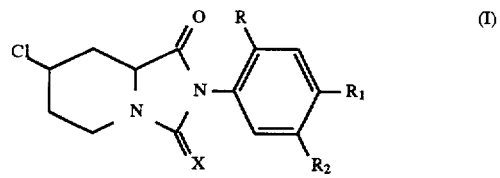

wherein
X is oxygen or sulfur,
R is hydrogen, chlorine or fluorine,
$R_1$ is fluorine, chlorine, bromine, cyano or methyl,
$R_2$ is halogen, $C_{1-6}$alkyl, $C_{1-6}$alkoxy, $C_{1-6}$alkylcarbonyloxy, $C_{3-6}$cycloalkoxy, $C_{3-6}$alkynyloxy, $C_{3-6}$alkenyloxy, —COOH, —CO—$R_3$, —CO—$NR_4R_5$, —$NR_6R_7$, $C_{2-6}$alkenyl, N-pyrrolyl, 2-oxo-3-tetrahydrofuranyl or is $C_{1-6}$alkyl substituted with halogen, COOH, —CO—$R_3$, —CO—$NR_8R_9$, =N—OH, =N—$C_{1-4}$alkoxy, —O—CO—$R_3$ or —O—$C_{2-3}$alkylene-O—; or is $C_{2-6}$alkenyl substituted with halogen, COOH, —CO—$R_3$, —CO—$NR_8R_9$ or $C_{1-4}$alkoxy; or is $C_{1-6}$alkoxy substituted with cyano, —CO—$R_3$, $C_{1-4}$alkoxy, $C_{3-6}$cycloalkyl, oxiranyl, or $C_{1-4}$alkoxy or halogen; or is $C_{3-6}$alkenyloxy substituted by $C_{2-5}$alkynyl;
$R_3$ is $C_{1-6}$alkyl, $C_{1-6}$haloalkyl, $C_{1-6}$cyanoalkyl, $C_{1-6}$alkoxy, $C_{3-6}$cycloalkoxy, $C_{3-6}$alkenyloxy, $C_{3-6}$alkynyloxy or $C_{1-6}$alkoxy substituted with cyano, halogen, $C_{1-6}$alkoxy, $C_{1-6}$alkoxycarbonyl, $C_{3-6}$alkynyloxycarbonyl or $C_{1-4}$alkoxy-$C_{1-4}$alkoxycarbonyl;
the use of such compounds for the control of phytopathogens, compositions for facilitating such use, and the preparation of the compounds of formula I.

7 Claims, No Drawings

2-PHENYL-7-CHLORO-PERHYDROIMIDAZO [1,5A]PYRIDINES

The present invention relates to novel 2-phenyl-7-chloro-perhydroimidazo[1,5a]pyridines, synthesis thereof, and the use of said compound for controlling undesired weeds.

Herbicidal 7-fluoro-perhydroimidazopyridines are known from EP-A-493 323 as effective compounds for combatting weeds. In practice however these compounds do not always satisfy the needs of selective weed control under all aspects, e.g. with respect to desired selectivity in crops of cultivated plants.

It has now been found that the 2-phenyl-7-chloro-perhydroimidazo[1,5a]pyridines of formula I

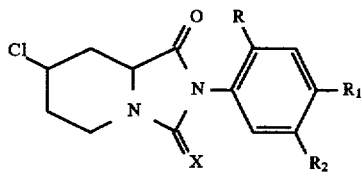 (I)

wherein
X is oxygen or sulfur,
R is hydrogen, chlorine or fluorine,
$R_1$ is fluorine, chlorine, bromine, cyano or methyl,
$R_2$ is halogen, $C_{1-6}$alkyl, $C_{1-6}$alkoxy, $C_{1-6}$alkylcarbonyloxy, $C_{3-6}$cycloalkoxy, $C_{3-6}$alkynyloxy, $C_{3-6}$alkenyloxy, —COOH, —CO—$R_3$, —CO—$NR_4R_5$, —$NR_6R_7$, $C_{2-6}$alkenyl, N-pyrrolyl, 2-oxo-3-tetrahydrofuranyl or a group

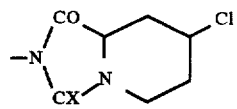

or is
$C_{1-6}$alkyl substituted with halogen, COOH, —CO—$R_3$, —CO—$NR_8R_9$, =N—OH, =N—$C_{1-4}$alkoxy, —O—CO—$R_3$ or —O—$C_{2-3}$alkylene-O—; or is
$C_{2-6}$alkenyl substituted with halogen, COOH, —CO—$R_3$, —CO—$NR_8R_9$ or $C_{1-4}$alkoxy; or is
$C_{1-6}$alkoxy substituted with cyano, —CO—$R_3$, $C_{1-4}$alkoxy, $C_{3-6}$cycloalkyl, oxiranyl, or optionally substituted thienyl or phenyl with the substituents selected from
$C_{1-4}$alkyl, $C_{1-4}$alkoxy or halogen; or is
$C_{3-6}$alkenyloxy substituted by $C_{2-5}$alkynyl; or
$R_1$ and $R_2$ together form a bridge member selected from —Y—$CHR_{10}$—CO—$NR_{11}$—, —O—$CH_2$—CO—$NR_{12}$—, —O—$CH_2$—$CH_2$—CZ— or —CH=CH—$NR_{13}$—,
$R_3$ is $C_{1-6}$alkyl, $C_{1-6}$haloalkyl, $C_{1-6}$cyanoalkyl, $C_{1-6}$alkoxy, $C_{3-6}$cycloalkoxy, $C_{3-6}$alkenyloxy, $C_{3-6}$alkynyloxy or $C_{1-6}$alkoxy substituted with cyano, halogen, $C_{1-6}$alkoxy, $C_{1-6}$alkoxycarbonyl, $C_{3-6}$alkynyloxycarbonyl or $C_{1-4}$alkoxy-$C_{1-4}$alkoxycarbonyl;
$R_4$ is hydrogen or $C_{1-4}$alkyl;
$R_5$ is $C_{1-4}$alkyl, $C_{3-4}$alkenyl, $C_{1-4}$alkynyl or $C_{1-4}$alkyl substituted with cyano, formyl or $C_{1-4}$alkoxycarbonyl;
$R_6$ is hydrogen or $C_{1-4}$alkyl;
$R_7$ is $C_{1-4}$alkylsulfonyl, $C_{1-4}$alkyl or $C_{1-4}$alkyl substituted by $C_{1-4}$alkoxycarbonyl;
$R_8$ is $C_{1-4}$alkyl;
$R_9$ is $C_{1-4}$alkyl, $C_{1-4}$cyanoalkyl, $C_{1-4}$alkoxy or $C_{3-4}$alkenyl; or $R_8$ and $R_9$ together form a $C_{4-5}$alkylene bridge or an ethylene-O-ethylene bridge, which bridge may be substituted with $C_{1-4}$alkyl or $C_{1-4}$alkoxycarbonyl;
$R_{10}$ is hydrogen or $C_{1-4}$alkyl;
$R_{11}$ is hydrogen, $C_{1-4}$alkyl, $C_{3-4}$alkenyl, $C_{3-4}$alkynyl, or $C_{3-4}$alkenyl substituted with halogen or $C_{1-4}$alkoxycarbonyl;
$R_{12}$ is $C_{1-4}$alkoxy;
$R_{13}$ is $C_{1-4}$alkyl, $C_{3-4}$alkenyl or $C_{3-4}$alkynyl,
Y is oxygen or sulfur, and
Z is oxygen or =N—$C_{1-4}$alkoxy,
are effective compounds for controlling undesired weeds.

The compounds of formula I have pronounced herbicidal activity against monocotyledonous and dicotyledonous weeds. A particularly high level of activity is observed against dicotyledonous weeds. Further, the compounds of formula I are well tolerated by most culture crop plants such as soybeans, sugarbeets, sunflower, and especially monocotyledonous crops such as sorghum, rice, maize and cereals, e.g. wheat barley, rye and oats.

In the above definitions under formula I the generic expressions designate the following more detailed chemical moieties.

Any alkyl group in the compound of formula I may be branched or straight chain and preferably has one to six carbon atoms, preferably one to four carbon atoms. Typical examples are methyl, ethyl, propyl, isopropyl, n-butyl, iso-butyl, see-butyl or tert. butyl.

Any alkenyl or alkynyl group may be either branched or straight chain and preferably has two to six carbon atoms. Examples are vinyl, allyl, methallyl, 2-butenyl, ethinyl, propargyl, 2-butinyl, 2-pentenyl, 3-pentenyl, 3-butinyl, or 2-pentinyl.

Halo or halogen as used herein, refers to chlorine, fluorine, bromine and iodine, with fluorine and chlorine being preferred.

Any cycloalkyl group preferably has three to six carbon ring atoms. Preferred examples are cyclopropyl, cyclopentyl or cyclohexyl.

The alkyl portion of alkoxy, haloalkyl or cyanoalkyl have the same designation as given for alkyl above. In particular, examples are methoxy, ethoxy, isopropoxy, propoxy, butyloxy, cyanomethyl, 2-cyanoethyl, 1-cyanoethyl, 1-cyano-1-methylethyl, 3-cyanopropyl, chloromethyl, 2,2, 2-trichloroethyl, trifluoromethyl, fluoromethyl, difluoromethyl, 1,1,2,2-tetrafluoroethyl, 2,2,2-trifluoroethyl, 2-chloroethyl or 2-fluoroethyl.

The carbons atom in 7-position and 8a-position of the perhydroimidazo[1,5a]pyridine ring system are asymmetrically substituted. The resulting products may therefore exist in diastereomeric forms. In most cases the product obtained from the given method of preparation will be in racemic form. The isomers may be separated by routine separation methods as known in the art. Additionally stereoselective routes of synthesis may provide predominantly the R- or S-form, depending on the employed starting materials. According to the present invention where not specially mentioned the compounds refer the mixtures as obtained from synthesis containing all isomers in varying ratios.

Among the compounds of formula I those are preferred wherein either
a) X is oxygen, or
b) R is fluorine, or
c) $R_1$ is chlorine, or
d) $R_1$ and $R_2$ together form the bridge —O—$CH_2$—$CONR_{11}$— or
e) $R_2$ is halogen, $C_{1-6}$alkoxycarbonyl-$C_{1-4}$alkyl or $C_{1-6}$alkoxycarbonyl-$C_{2-6}$alkenyl.

In an especially preferred subgroup of formula I X is oxygen, R is fluorine, $R_1$ is chlorine and $R_2$ is halogen, $C_{1-6}$alkoxycarbonyl-$C_{1-4}$alkyl or $C_{1-6}$alkoxycarbonyl-$C_{2-4}$alkenyl.

Preferred individual compounds of formula I are: 7-chloro-2-(5-bromo-4-chloro-2-fluorophenyl)-perhydroimidazo[1,5a]pyridine-1,3-dione; methyl β-[2-chloro-4-fluoro-5-(7-chloro-perhydroimidazo[1,5a]pyridine-1,3-dione-2-yl)phenyl]-propionate; and methyl 2-chloro-4-fluoro-5-(7-chloro-perhydroimidazo[1,5a]pyridine-1,3-dione-2-yl)cinnamate.

Compounds of the formula I are useful because they demonstrate herbicidal activity, combined with excellent selectivity in cultivated crop plants.

Compounds of the formula I may be obtained from an intramolecular condensation of a compound of formula II

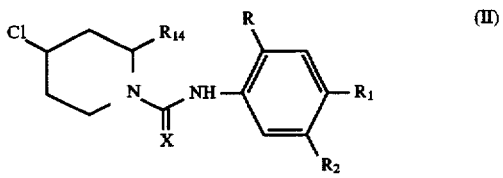

wherein
X, n, R, $R_1$ and $R_2$ are as defined for formula I and
$R_{14}$ is COOH, COOW or COSW, and
W is $C_{1-4}$alkyl.

This condensation reaction is carried out under conditions that are typical for preparing hydantoin compounds. The reaction is facilitated by the presence of an acid or an alkaline agent. The condensation reaction may be carried out under acidic or alkaline conditions. Accordingly, the reaction may be carried out in an inert medium such as toluene in the presence of an alkaline agent such as triethylamine. Suitable temperatures range from about room to 60° C., preferably about 50° C. The resulting product is isolated and purified in accordance with known processes such as extraction and crystallization.

Compounds of the formula II may be prepared by reacting a compound of the formula III

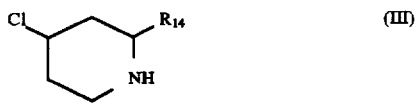

wherein $R_{14}$ is defined under formula II with a substituted phenyl isocyanate or isothiocyanate of formula IV

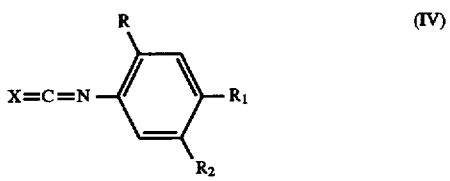

wherein R, $R_1$, $R_2$ and X are as defined under formula II.

This reaction may be carried out in an inert medium such as toluene, preferably at ambient temperature. The resulting compound of formula II can be recovered from solution by standard separation techniques, e.g. suction filtration and chromatography.

The substituted phenyl isocyanates or isothiocyanates of formula IV are known. Compounds of the formula III are either known or can be prepared from known compounds according to known procedure. (c.f. Tetrahedron, Vol. 47(24), 4039–4062, 1991).

The compounds of formula I are effective in controlling the growth of plants. By plants it is meant germinating seeds, emerging seedlings and established vegetation including underground portions. In particular, the compounds are useful as herbicides as indicated by causing damage to both monocotyledonous and dicotyledonous plants in various standard evaluations for determining such effects. The herbicidal effects are exhibited both pre- and post-emergence the plants. Such herbicidal effects indicate that the compounds of formula I are particularly of interest in combatting and controlling weeds (unwanted plants).

The compounds of the formula I are indicated mainly to be stronger acting against dicotyledonous plants than monocotyledonous plants. Relatively less toxicity towards crops than towards weeds is further indicated. Hence, the compounds are of particular interest as selective herbicides to combat weeds in a crop locus, particularly as locus of a crop such as, for example, sugarbeet, sunflower, cotton, soybean, rice, maize and cereals, e.g. wheat, barley, rye and oats, but especially wheat.

The present invention therefore also provides a method of combatting weeds in a locus which comprises applying to the weeds or their locus a herbicidally effective amount of a compound of the invention. When selective action is desired in crop locus, the amount applied will be sufficient to combat weeds without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation in application, the various conditions of treatment such as soil and weather and the like. However, in general, satisfactory results in weed control are usually obtained upon application of the compounds of the invention at a rate in the range of from 0.001 to 2 kg/hectare, more usually 0.01 to 1 kg/hectare, and preferably 0.01 to 0.25 kg/hectare, the application being repeated as necessary. When used in crops, the application usually will not exceed about 1 kg/hectare, and is usually in the range of 0.01 to 0.5 kg/hectare.

For practical use as herbicides, the compounds of formula I may be and are preferably employed in herbicidal compositions comprising a herbicidal effective amount of the compound and an inert carrier which is agriculturally acceptable in the sense of not, by reason of its presence, poisoning the agricultural environment including the immediate soil of application or any crops present therein or otherwise being unsafe for application. Such compositions of formulations may contain 0.01% to 99% by weight of active ingredient, from 0 to 20% by weight of agriculturally acceptable surfactants and 1 to 99.99% by weight of the inert carrier. Higher ratios of surfactant to active ingredient are sometimes desirable and are achieved by incorporation into the formulation or by tank mixing. Application forms of composition typically contain between 0.01 and 25% by weight of active ingredient, but lower or higher levels of active ingredient can, of course, be present depending on the intended use and the physical properties of the compounds. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained by conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compound with a solid inert carrier such as talc, clay, silica and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Alternatively, the compounds of the invention may be used in micro-encapsulated form.

Agriculturally acceptable additives may be employed in the herbicidal compositions to improve the performance of the active ingredient and to reduce foaming, caking and corrosion.

Surfactant as used herein means agriculturally acceptable material which imparts emulsifiability, spreading, wetting, disperibility or other surface-modifying properties. Examples of surfactants are sodium lignin sulphonate and lauryl sulphate.

Carriers as used herein mean a liquid or solid material used to dilute a concentrated material to a usable or desirable strength. For dusts or granules it can be e.g. talc, kaolin or diatomaeous earth, for liquid concentrate forms, a hydrocarbon such as xylene or an alcohol such as isopropanol; and for liquid application forms, e.g. water or diesel oil.

The compositions of this application can also comprise other compounds having biological activity, e.g. compounds having similar or complementary herbicidal activity or compounds having antidotal, fungicidal or insecticidal activity.

Typical herbicidal composition, according to this invention, are illustrated by the following Examples A, B and C in which the quantities are in parts by weight.

EXAMPLE A

Preparation of a Dust

10 Parts of a compound of formula I and 90 parts of powdered talc are mixed in a mechanical grinder-blender and are ground until a homogenous, free flowing dust of the desired particle size is obtained. This dust is suitable for direct application to the site of the weed infestation.

EXAMPLE B

Preparation of Wettable Powder

25 Parts of a compound of formula I are mixed and milled with 25 parts of synthetic fine silica, 2 parts of sodium lauryl sulphate, 3 parts of sodium lignin sulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

13 Parts of a compound of formula I are mixed in a beaker with 7 parts of Toximul 360A (a mixture of anionic and non-ionic surfactants containing largely non-ionic surfactants), 24 parts of dimethylformamide and 56 parts of Tenneco 500-100 (predominantly a mixture of alkylated aromatics such as xylene and ethylbenzene) until solution is effected. The resulting EC is diluted with water for use.

EXAMPLE 1

Methyl 2-chloro-4-fluoro-5-(7-chloro-perhydroimidazo[1,5a]pyridine-1,3-dione-2-yl) cinnamate

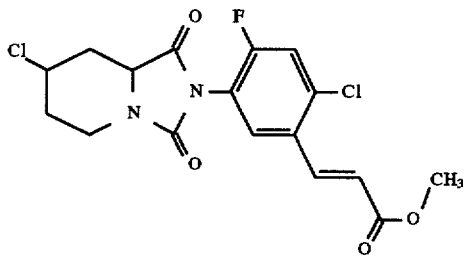

To a solution of 38.5 g (0.18 mol)4-chloro-2-piperidine carboxylic acid methyl ester hydrochloride and 40 g (0.396 mol) triethylamine in 1200 ml $CH_2Cl_2$ is added in small portions 46 g (0.18 mol) isocyanate of methyl 2-chloro-4-fluoro-5-amino-cinnamate dissolved in 300 ml $CH_2Cl_2$. The reaction solution is stirred at room temperature for a period of 20 hours, washed with 2×500 ml water, dried with $Na_2SO_4$ and the solvent is evaporated. The residual brown syrup is treated with 500 ml ether/hexane (4:1) affording methyl 2-chloro-4-fluoro-5-(7-chloro-perhydroimidazo[1,5] pyridine-1,3-dione-2-yl) cinnamate as a white powder with m.p. of 162°–163° C.

The compounds of the following tables are obtained in analogous manner.

TABLE 1

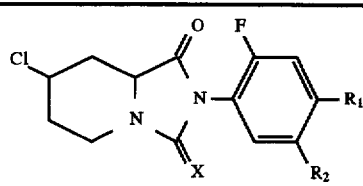

| No. | $R_1$ | $R_2$ | X | mp. or Rf on $SiO_2$ |
|---|---|---|---|---|
| 1.01 | $CH_3$ | $COOCH(CH_3)_2$ | O | 130–131° C. |
| 1.02 | Cl | $COOCH_3$ | O | 0,12 HXF/EST 7:3 |
| 1.03 | Cl | $COOCH_2CH_3$ | O | 82–85° C. |
| 1.04 | Cl | $COOCH_2CN$ | O | 176–178° C. |
| 1.05 | Cl | $COOCH_2CH_2CH_3$ | O | 0.21 HXF/EST 7:3 |
| 1.06 | Cl | $COOCH_2CH_2CH_2CH_3$ | O | 0.23 HXF/EST 7:3 |
| 1.07 | Cl | $COOCH(CH_3)CH_2CH_3$ | O | 0.26 HXF/EST 7:3 |

TABLE 1-continued

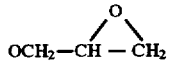

| No. | $R_1$ | $R_2$ | X | mp. or Rf on $SiO_2$ |
|---|---|---|---|---|
| 1.08 | Cl | $COOC(CH_3)_3$ | O | 157° C. |
| 1.09 | Cl | $COOCH_2CH(CH_3)_2$ | O | 0.26 HXF/EST 7:3 |
| 1.10 | Cl | $COOCH_2CH_2OCH_2CH_3$ | O | 0.28 HXF/EST 1:1 |
| 1.11 | Cl | $COOCH(CH_3)CH_2OCH_3$ | O | 0.11 HXF/EST 7:3 |
| 1.12 | Cl | $COO-C_5H_9$-cycl. | O | 0.23 HXF/EST 7:3 |
| 1.13 | Cl | $COO(CH_2)_4CH_3$ | O | 0.27 HXF/EST 7:3 |
| 1.14 | Cl | $COOC(CH_3)_2CH=CH_2$ | O | 0.24 HXF/EST 7:3 |
| 1.15 | Cl | $COOCH_2CH_2OCH_3$ | O | 0.27 HXF/EST 1:1 |
| 1.16 | Cl | $COOCH(CH_3)-CN$ | O | 0.10 HXF/EST 7:3 |
| 1.17 | Cl | $COOCH_2CH=CH_2$ | O | 123–125° C. |
| 1.18 | Cl | $COOCH_2C\equiv CH$ | O | 128–130° C. |
| 1.19 | Cl | $COOCH_2-C(CH_3)=CH_2$ | O | 0.15 SE/EST 1:1 |
| 1.20 | Cl | $COOCH_2CH=CH-CH_3$ | O | 0.17 SE/EST 1:1 |
| 1.21 | Cl | $COOCH(CH_3)_2$ | O | 0.22 HXF/EST 7:3 |
| 1.22 | Cl | $COOCH(CH_3)-CH(CH_3)_2$ | O | 0.35 HXF/EST 7:3 |
| 1.23 | Cl | $COOCH(CH_3)CH_2CH_2CH_3$ | O | 0.36 HXF/EST 7:3 |
| 1.24 | Cl | $COOCH(CH_3)CH_2CH=CH_2$ | O | 0.23 HXF/EST 7:3 |
| 1.25 | Cl | $COOCH(CH_3)CH_2COOCH_3$ | O | 0.10 HXF/EST 7:3 |
| 1.26 | Cl | $COOCH(CH_3)CH_2CH(CH_3)_2$ | O | 0.27 HXF/EST 7:3 |
| 1.27 | Cl | $COOCH(CH_3)CH_2CH_2CH_2CH_3$ | O | 0.28 HXF/EST 7:3 |
| 1.28 | Cl | $COOC(CH_3)_2-CN$ | O | 58° C. |
| 1.29 | Cl | COOH | O | 196–199° C. |
| 1.30 | Cl | $COOCH_3$ | S | 149–151° C. |
| 1.31 | Cl | $COOCH_2CH_3$ | S | 161–162° C. |
| 1.32 | Cl | $COOCH(CH_3)_2$ | S | 163–165° C. |
| 1.33 | Cl | $COOCH_2CH_2OCH_3$ | S | 138–140° C. |
| 1.34 | Cl | $COCH(CH_3)CH_2OCH_3$ | S | 111–113° C. |
| 1.35 | Cl | $CON(CH_3)-CH(CH_3)_2$ | O | 166–168° C. |
| 1.36 | Cl | $CON(CH_3)_2$ | O | 185–187° C. |
| 1.37 | Cl | $CONH(CH_2)_3CH_3$ | O | 0.15 HXF/EST 1:1 |
| 1.38 | Cl | $CONHC(CH_3)_3$ | O | 0.30 HXF/EST 1:1 |
| 1.39 | Cl | $CON(CH_3)-(CH_2)_3CH_3$ | O | 0.10 HXF/EST 1:1 |
| 1.40 | Cl | $CON(CH_3)CH_2CH_2C\equiv N$ | O | 0.08 HXF/EST 3:7 |
| 1.41 | Cl | $CON(CH_3)CH_2C\equiv CH$ | O | 0.18 HXF/EST 1:1 |
| 1.42 | Cl | $CON(CH_2CH_3)_2$ | O | 0.22 HXF/EST 3:7 |
| 1.43 | Cl | $CON(CH_3)CH_2COOCH_3$ | O | 0.20 HXF/EST 3:7 |
| 1.44 | Cl | $CON(CH_3)CH_2CH=O$ | O | 0.07 HXF/EST 3:7 |
| 1.45 | Br | $OCH_3$ | O | 116–119° C. |
| 1.46 | Br | $OCH_2CH_3$ | O | 209–211° C. |
| 1.47 | Br | $OCH_2CH=CH-Cl$ | O | 205–208° C. |
| 1.48 | Br | $O(CH_2)_3CN$ | O | 59–62° C. |
| 1.49 | Cl | O-benzyl | O | 256–258° C. |
| 1.50 | Cl | $OCH(CH_3)_2$ | S | 134° C. |
| 1.51 | Cl | $OCH(CH_3)_2$ | O | 96–98° C. |
| 1.52 | Cl | $OCH_2CH_2OCH_3$ | O | 111–113° C. |
| 1.53 | Cl | $OCH_2CH_2OCH_2CH_3$ | O | 0.17 HXF/EST 1:1 |
| 1.54 | Cl | $OCH(CH_3)-C\equiv CH$ | O | 142–144° C. |
| 1.55 | Cl | $OCH_2C\equiv CH$ | O | 179–181° C. |
| 1.56 | Cl | $OCH_2CH=CH_2$ | O | 0.17 HXF/EST 7:3 |
| 1.57 | Cl | $OCH_2-C_3H_5$-cycl. | O | 59–60° C. |
| 1.58 | Cl | 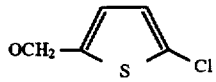 $OCH_2-CH-CH_2$ (epoxide) | O | 63° C. |
| 1.59 | Cl | $OCH_2$-(thienyl-Cl) | O | 173–175° C. |
| 1.60 | Cl | $OCH_2CH=CH-C\equiv C-C(CH_3)_3$ | O | 0.24 HXF/EST 7:3 |
| 1.61 | Cl | $-O-C_5H_9$-cycl. | O | 0.38 HXF/EST 2:8 |
| 1.62 | CN | $OCH_2CH_3$ | O | 290–292° C. |

TABLE 1-continued

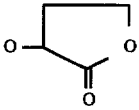

| No. | R₁ | R₂ | X | mp. or Rf on SiO₂ |
|---|---|---|---|---|
| 1.63 | CN | F | O | 265–268° C. |
| 1.64 | CH₃ | OCH₂COO(CH₂)₄CH₃ | O | 82° C. |
| 1.65 | Cl | OCH₂COOCH₃ | O | 0.24 HXF/EST 1:1 |
| 1.66 | Cl | OCH₂COOCH₂CH₃ | O | 0.22 SE/HXF 8:2 |
| 1.67 | Cl | OCH₂COOCH₂CH₂CH₃ | O | 0.20 SE/HXF 7:3 |
| 1.68 | Cl | OCH₂COOCH(CH₃)₂ | O | 0.16 SE/HXF 7:3 |
| 1.69 | Cl | OCH₂COO(CH₂)₃CH₃ | O | 0.21 SE/HXF 7:3 |
| 1.70 | Cl | OCH₂COO(CH₂)₄CH₃ | O | 0.45 HXF/EST 1:1 |
| 1.71 | Cl | OCH(CH₃)COOCH₃ | O | 0.20 SE/HXF 8:2 |
| 1.72 | Cl | OCH(CH₃)COOCH₂CH₃ | O | 0.13 HXF/EST 7:3 |
| 1.73 | Cl | OCH(CH₃)COOCH₂CH₂CH₃ | O | 0.15 HXF/EST 7:3 |
| 1.74 | Cl | OCH(CH₃)COOCH(CH₃)₂ | O | 0.27 SE/HXF 7:3 |
| 1.75 | Cl |  Isomer 1<br>Isomer 2 | O<br>O | 0.38 EST<br>0.43 EST |
| 1.76 | Cl | OCOC(CH₃)₃ | O | 0.16 SE/HXF 1:1 |
| 1.77 | Cl | OCH₂OCOC(CH₃)₃ | O | 0.17 SE/HXF 1:1 |
| 1.78 | Cl | CH(CH₃)₂ | O | 146–148° C. |
| 1.79 | Cl | CH₂OCH₂COOCH₃ | O | 0.06 HXF + 2.5% EST |
| 1.80 | Cl | CH₂OCOCH₃ | O | 0.37 HXF/EST 1:1 |
| 1.81 | Cl | CH₂OCOCH₂CH₃ | O | 0.07 HXF + 20% EST |
| 1.82 | Cl | CH₂OCOCH(CH₃)₂ | O | 0.10 HXF + 30% EST |
| 1.83 | Cl | CH₂OCOCH₂Cl | O | 0.08 HXF + 30% EST |
| 1.84 | CH₃ | CH(CH₃)OCOCH₃ | O | 0.15 HXF + 30% EST |
| 1.85 | CH₃ | CH₂CH₃ | O | 0.1 HXF + 2.5% EST |
| 1.86 | Cl | Br | O | 177–179° C. |
| 1.87 | Cl | J | O | 183–184° C. |
| 1.88 | Br | OCH₂—C(CH₃)₃ | O | 282–284° C. |
| 1.89 | Cl | NH—CH₃ | O | 0.17 HXF/EST 6:4 |
| 1.90 | Cl | N(CH₃)₂ | O | 0.26 SE |
| 1.91 | Cl | 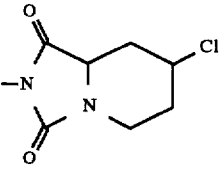 | O | 0.15 SE/HXF 1:1 |
| 1.92 | Cl | 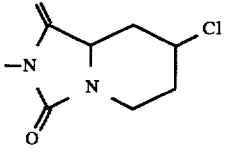 | O | 0.11 EST/HXF 1:1 |
| 1.93 | F | (same as 1.92) | O | 0.13 EST/HXF 1:1 |
| 1.94 | Cl | —CH═CH—COOH | O | 239–242° C. |
| 1.95 | Cl | —CH═CH—COOCH₃ | O | 162–163° C. |
| 1.96 | Cl | —CH═CH—COOCH₂CH₃ | O | 76–78° C. |
| 1.97 | Cl | —CH═CH—COOCH₂CH₂CH₃ | O | 75–77° C. |
| 1.98 | Cl | —CH═CH—COOCH(CH₃)₂ | O | 78–80° C. |
| 1.99 | Cl | —CH═CH—COOCH(CH₃)CH₂CH₃ | O | 121–122° C. |
| 1.100 | Cl | —CH═CH—COO(CH₂)₄CH₃ | O | 86–88° C. |

TABLE 1-continued

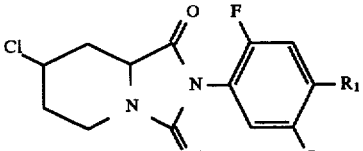

| No. | R₁ | R₂ | X | mp. or Rf on SiO₂ |
|---|---|---|---|---|
| 1.101 | Cl | —CH=CH—COOCH—CH₃ <br>                                   | <br>                         COOCH—CH₃ <br>                                 | <br>                           CH₂—OCH₃ | O | 88–89° C. |
| 1.102 | Cl | —CH=CH—COOCH(CH₃)COOCH₂C≡CH | O | 123–125° C. |
| 1.103 | Cl | —CH=CH—COOCH₂COOCH₂CH(CH₃)₂ | O | 72–74° C. |
| 1.104 | Cl | —CH=CH—COCH₃ | O | 152–153° C. |
| 1.105 | Cl | —CH=CH—CH(CH₃)—OCH₃ | O | 112–114° C. |
| 1.106 | Cl | —CH=CH—CON(CH₃)—CH(CH₃)₂ | O | 202–204° C. |
| 1.108 | Cl | —CH=CH—CON[CH(CH₃)₂]₂ | O | 167–168° C. |
| 1.109 | Cl | —CH=CH—CON(CH₃)CH₂CH₂C≡N | O | 196–197° C. |
| 1.110 | Cl |  | O | 128–130° C. |
| 1.111 | Cl | 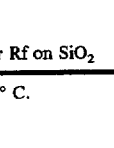 | O | 136–138° C. |
| 1.112 | Cl | 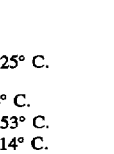 | O | 237–238° C. |
| 1.113 | Cl | —CH=CH—CON(CH₃)OCH₃ | O | 170–172° C. |
| 1.114 | Cl | —CH₂—CH₂COOH | O | 174–172° C. |
| 1.115 | Cl | CH₂CH₂—COOCH₃ | O | 110–112° C. |
| 1.116 | Cl | CH₂—CHCl—COOCH₃ | O | 0.33 EST/HXF 1:1 |
| 1.117 | Cl | CH₂CH₂—COOCH₂CH₃ | O | 0.40 EST/HXF 1:1 |
| 1.118 | Cl | CH₂CH₂—COOCH₂CH₂CH₃ | O | 0.36 EST/HXF 1:1 |
| 1.119 | Cl | CH₂CH₂—COOCH(CH₃)₂ | O | 0.48 EST/HXF 2:1 |
| 1.120 | Cl | CH₂CH₂—COOCH(CH₃)CH₂CH₃ | O | 0.38 EST/HXF 1:1 |
| 1.121 | Cl | CH₂CH₂COCH₃ | O | 163–165° C. |
| 1.122 | Cl | CH₂CH₂C(CH₃)=NOH | O | 95–96° C. |
| 1.123 | Cl | CH₂CH₂C(CH₃)=NOCH₃ | O | 104–105° C. |
| 1.124 | Cl | 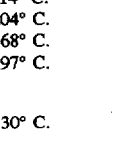 | O | 149–150° C. |
| 1.125 | Cl | 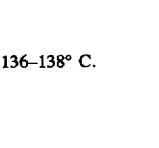 | O | 0.11 EST |
| 1.126 | Cl | 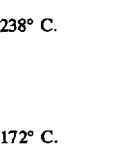 | O | 0.26 EST |
| 1.127 | Cl | 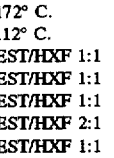 | O | 0.15 EST |
| 1.128 | Cl | CH₂CH₂—CON(CH₃)CH₂CH₂CN | O | 0.20 EST |
| 1.129 | Cl | CH₂CH₂—CON(CH₃)CH₂CH=CH₂ | O | 0.28 EST |

TABLE 1-continued

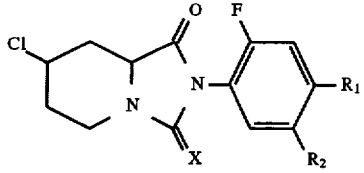

| No. | R₁ | R₂ | X | mp. or Rf on SiO$_2$ |
|---|---|---|---|---|
| 1.130 | Cl | CH$_2$CH$_2$CO—N⟨piperidine⟩—COOCH$_2$CH$_3$ | O | 0.32 EST |
| 1.131 | Cl | CH$_2$CH$_2$CO—N⟨piperidine, COOCH$_2$CH$_3$⟩ | O | 0.31 EST |
| 1.132 | Cl | CH$_2$CH$_2$CO—N⟨2,6-diMe-piperidine⟩ | O | 0.39 EST |
| 1.133 | Cl | CH$_2$CH$_2$CON⟨2,2-diMe + CH$_3$ piperidine⟩ | O | 0.35 EST |
| 1.134 | Cl | CH$_2$CH(CH$_3$)CH$_2$Cl | O | 88–90° C. |
| 1.135 | Cl | —CH=CCl—COOCH$_3$ | O | |
| 1.136 | Cl | —CH=CCl—COOC$_2$H$_5$ | O | |
| 1.137 | Cl | NH—CH$_2$—COOCH$_3$ | O | |
| 1.138 | Cl | NH—CH(CH$_3$)—COOCH$_3$ | O | |
| 1.139 | Cl | N(CH$_3$)—CH$_2$—COOCH$_3$ | O | |
| 1.140 | Cl | N(CH$_3$)—CH(CH$_3$)—COOCH$_3$ | O | |
| 1.141 | Cl | N(CH$_3$)—SO$_2$—CH$_3$ | O | |
| 1.142 | Cl | N(CH$_3$)—SO$_2$—C$_2$H$_5$ | O | |
| 1.143 | Br | O—CH$_2$—C(CH$_3$)=CH$_2$ | O | 0.2 EST/HXF 3:7 |

HXF = hexane
EST = ethyl acetate
SE = diethyl ether

TABLE 2

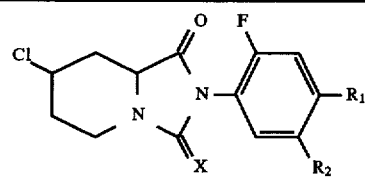

| No. | R₁ + R₂ | X | m.p. or Rf on SiO$_2$ |
|---|---|---|---|
| 2.01 | —O—CH$_2$—CO—NH— | S | 223–224° C. |
| 2.02 | —O—CH$_2$—CO—N(CH$_2$C≡CH)— | O | 198–200° C. |
| 2.03 | —O—CH$_2$—CO—N(CH$_2$CH=CH$_2$)— | O | 208–109° C. |

TABLE 2-continued

[Structure: chlorinated piperidine fused with imidazolinone bearing 2-fluoro-4-R1-5-R2-phenyl group, with X substituent]

| No. | R₁ + R₂ | X | m.p. or Rf on SiO₂ |
|---|---|---|---|
| 2.04 | —O—CH₂—CO—N(—CH₂C≡CH) | S | 146–148° C. |
| 2.05 | —OCH(CH₃)—CO—N(—CH₂C≡CH) | O | 130–134° C. |
| 2.06 | —S—CH₂—CO—N(—CH₂C≡CH) | O | 243–244° C. |
| 2.07 | —O—CH₂—CO—N(—CH₂—C(CH₃)=CH₂) | O | 165–167° C. |
| 2.08 | —O—CH₂—CO—N(—CH₂—C(Br)=CH₂) | O | 210–211° C. |
| 2.09 | —O—CH₂—CO—N(—CH₂CH=CH—COOCH₃) | O | 240–242° C. |
| 2.10 | —O—CH₂—CO—N(—CH₂CH=CH—Br) | O | 206–208° C. |
| 2.11 | —O—CH₂—CO—N(—CH₂CH=CH—CH₃) | O | 163–165° C. |
| 2.12 | —O—CH₂—CO—N(—CH₂—C(Cl)=CH₂) | O | 208–210° C. |
| 2.13 | —O—CH₂CO—N(—CH₂CH₃) | O | 214–216° C. |
| 2.14 | —O—CH₂—CO—N(—CH₃) | O | 239–240° C. |
| 2.15 | —O—CH₂—CH₂—CO— | O | 213–214° C. |
| 2.16 | —O—CH₂—CH₂—C(=NOCH₃) | O | 169° C. |
| 2.17 | —O—CH₂—CO—N(—OCH₂CH₃) | O | 221° C. |
| 2.18 | —CH=CH—N(—CH₂C≡CH) | O | 172–173° C. |

Biological Test

Example H1

Post-emergence Herbicidal Activity

Pots filled with a sandy loam type of soil are sown with 14 dicotyledonous weeds and kept under standard germination conditions in a greenhouse.

When the plants have about 2 leaves they are sprayed at 3 or 4 rates (5.5, 16.6, 50 and 150 g ai/ha) with a spray volume of 600 l/ha. The pots are watered as needed from above. The herbicidal activity is visually estimated (0–100%, in comparison to an untreated control) 25 days after application.

In this test the compounds of formula I exhibited good herbicidal activity. Compounds 1.17, 1.22, 1.25, 1.31, 1.38, 1.61, 1.63, 1.68, 1.72, 1.86, 1.110, 1.113, 1.117, 1.126, 1.143 and 2.14 showed more than 90% efficacy at an application rate of 50 g ai./ha under the test conditions.

Example H2

Comparative Test

In a postemergence test carried out in a green house pots were filled with a sandy loam type of soil are sown with *Abutilon theophrasti, Galium aparine, Ipomoea purpurea, Matricaria chamomilla, Portulaca oleracea, Senecio vulgaris, Solanum nigrum, Stellaria media, Xanthium strumarium*, maize and wheat. When the plants have about 2 leaves they are sprayed at rates of 16.6 g ai/ha with a spray volume of 600 l/ha. The pots are watered as needed from above. The herbicidal activity is visually estimated (0–100%, in comparison to an untreated control) 25 days after application.

In order to compare efficacy and selectivity of the compounds of present invention to the compounds of EP-A493 323 representative species were tested in the above test procedure.

The tested compounds were:

Compounds 1.08, 1.21 and 1.51 from present application and compounds A (known from EP-A-493323 as compound 1.53), B (known from EP-A-493323 as compound 1.34), and C (known from EP-A-493323 as compound 1.51).

The chemical designations of the test compounds are:
Compound 1.08: tert. butyl 2-chloro-4-fluoro-5-(7-chloro-perhydroimidazo[1,5a]pyridine-1,3-dione-2-yl)benzoate,
Compound A: tert.butyl 2-chloro-4-fluoro-5-(7-fluoro-perhydroimidazo[1,5a]pyridine-1,3-dione-2-yl)benzoate,
Compound 1.21: isopropyl 2-chloro-4-fluoro-5-(7-chloro-perhydroimidazo[1,5a]pyridine-1,3-dione-2-yl)benzoate,
Compound B: isopropyl 2-chloro-4-fluoro-5-(7-fluoro-perhydroimidazo[1,5a]pyridine-1,3-dione-2-yl)benzoate,
Compound 1.51: 7-chloro-2-(4-chloro-2-fluoro-5-isopropoxyphenyl)perhydroimidazo[1,5a]pyridine-1,3-dione,
Compound C: 7-fluoro-2-(4-chloro-2-fluoro-5-isopropoxyphenyl)perhydroimidazo[1,5a]pyridine-1,3-dione.

The following test results were obtained (plant damage in %):

a) post-emergence: maize, Variety Mutin
application rate 16.6 g a.i./ha.

| plant | Compound 1.08 | Compound A |
|---|---|---|
| maize | 0 | 20 |
| abutilon | 100 | 100 |
| chenopodium | 100 | 100 |
| ipomoea | 100 | 90 |
| portulaca | 100 | 100 |
| solanum | 100 | 100 |
| xanthium | 100 | 100 |

| plant | Compound 1.21 | Compound B |
|---|---|---|
| maize | 20 | 40 |
| abutilon | 100 | 100 |
| chenopodium | 100 | 100 |
| ipomoea | 100 | 100 |
| portulaca | 100 | 100 |
| solanum | 100 | 100 |
| xanthium | 100 | 100 |

| plant | Compound 1.51 | Compound C |
|---|---|---|
| maize | 20 | 70 |
| abutilon | 100 | 100 |
| chenopodium | 100 | 100 |
| ipomoea | 100 | 100 |
| portulaca | 100 | 100 |
| solanum | 100 | 100 |
| xanthium | 100 | 100 | b) post-emergence: wheat, Variety Albis
application rate 16.6 g a.i./ha

| plant | Compound 1.08 | Compound A |
|---|---|---|
| wheat | 80 | 100 |
| chenopodium | 100 | 100 |
| galium | 100 | 80 |
| matricaria | 100 | — |
| senecio | 95 | 80 |
| stellaria | 100 | 100 |

| plant | Compound 1.21 | Compound B |
|---|---|---|
| wheat | 30 | 40 |
| chenopodium | 100 | 100 |
| galium | 100 | 100 |
| matricaria | 100 | — |
| senecio | 100 | 100 |
| stellaria | 100 | 100 |

| plant | Compound 1.51 | Compound C |
|---|---|---|
| wheat | 20 | 70 |
| chenopodium | 100 | 100 |
| galium | 100 | 100 |
| matricaria | 100 | 90 |
| senecio | 80 | 90 |
| stellaria | 100 | 40 |

From all comparative tests it is evident that the chloro-compounds of present invention are better tolerated by maize and wheat plants than the fluoro-compounds known from the prior art. For practical applications in wheat compound 1.08 will require application rates lower than the tested rate.

We claim:
1. A compound of formula I

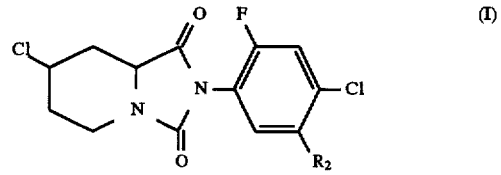

wherein
$R_2$ is halogen, $C_{1-6}$alkyl, $C_{1-6}$alkoxy, $C_{1-6}$alkylcarbonyloxy, $C_{1-6}$alkoxycarbonyl, $C_{1-6}$alkoxycarbonyl-$C_{1-4}$alkyl or $C_{1-6}$alkoxycarbonyl-$C_{2-4}$alkenyl.

2. A compound selected from the group consisting of
7-chloro-2-(5-bromo-4-chloro-2-fluorophenyl)-perhydroimidazo[1,5a]pyridine-1,3-dione;

methyl β-[2-chloro-4-fluoro-5-(7-chloro-perhydroimidazo[1,5a]pyridine-1,3-dione-2-yl)-phenyl]-propionate; and methyl 2-chloro-4-fluoro-5-(7-chloro-perhydroimidazo[1,5a]pyridine-1,3-dione-2-yl)cinnamate.

3. A herbicidal composition comprising a compound of formula I according to claim 1 and an agriculturally acceptable carrier.

4. A method of combatting weeds which comprises applying to the weeds or their locus a herbicidally effective amount of a compound of formula I according to claim 1.

5. The compound according to claim 1 selected from the group consisting of tert.butyl-2-chloro-4-fluoro-5-(7-chloro-perhydroimidazo[1,5a]pyridine-1,3-dione-2-yl) benzoate, isopropyl 2-chloro-4-fluoro-5-(7-chloro-perhydroimidazo[1,5a]pyridine-1,3-dione-2-yl)benzoate and 7-chloro-2-(2-fluoro-4-chloro-5-isopropoxyphenyl)-perhydroimidazo[1,5a]pyridine-1,3-dione.

6. A herbicidal composition comprising a compound according to claim 2 and an agriculturally acceptable carrier.

7. A method of combating weeds which comprises applying to the weeds or their locus a herbicidally effective amount of a compound according to claim 2.

* * * * *